(12) United States Patent
Ginn et al.

(10) Patent No.: US 6,277,140 B2
(45) Date of Patent: *Aug. 21, 2001

(54) VASCULAR SHEATH WITH PUNCTURE SITE CLOSURE APPARATUS AND METHODS OF USE

(75) Inventors: Richard S. Ginn, San Jose; William N. Aldrich, Los Altos Hills, both of CA (US)

(73) Assignee: Integrated Vascular Systems, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/764,813

(22) Filed: Jan. 16, 2001

Related U.S. Application Data

(63) Continuation of application No. 09/478,179, filed on Jan. 5, 2000.

(51) Int. Cl.[7] ............................................. A61B 17/04
(52) U.S. Cl. .................... 606/213; 606/139; 606/142; 606/219
(58) Field of Search .................... 606/213, 139, 606/142, 144, 148, 214; 227/175.1, 179.1

(56) References Cited

U.S. PATENT DOCUMENTS

| | | |
|---|---|---|
| 3,586,002 | 6/1971 | Wood . |
| 3,604,425 | 9/1971 | Le Roy ................................. 128/325 |
| 3,757,629 | 9/1973 | Schneider ............................... 85/49 |
| 3,805,337 | 4/1974 | Branstetter ............................... 24/27 |
| 4,192,315 | 3/1980 | Hilzinger et al. ..................... 128/346 |
| 4,217,902 | 8/1980 | March .................................. 128/325 |
| 4,396,139 | 8/1983 | Hall et al. .............................. 227/19 |
| 4,485,816 | 12/1984 | Krumme ............................. 128/334 |
| 4,505,274 | 3/1985 | Speelman ............................ 606/219 |
| 4,586,503 | 5/1986 | Kirsch et al. ........................ 128/334 |
| 4,777,950 | 10/1988 | Kees, Jr. .............................. 128/325 |
| 4,860,746 | 8/1989 | Yoon .................................... 128/326 |
| 4,865,026 | 9/1989 | Barrett ................................. 606/213 |
| 4,917,087 | 4/1990 | Walsh et al. ......................... 606/153 |
| 4,950,258 | 8/1990 | Kawai et al. ........................ 606/213 |
| 5,007,921 | 4/1991 | Brown ................................. 606/221 |
| 5,026,390 | 6/1991 | Brown ................................. 606/221 |
| 5,053,008 | 10/1991 | Bajaj ................................... 604/104 |
| 5,061,274 | 10/1991 | Kensey ................................ 606/213 |
| 5,108,420 | 4/1992 | Marks .................................. 606/213 |
| 5,156,609 | 10/1992 | Nakao et al. ........................ 606/142 |
| 5,176,648 | 1/1993 | Holmes et al. ...................... 604/164 |
| 5,192,302 | 3/1993 | Kensey et al. ....................... 606/213 |

(List continued on next page.)

FOREIGN PATENT DOCUMENTS

| | | | |
|---|---|---|---|
| WO 97/20505 | 6/1997 | (WO) | ............................. A61B/17/00 |
| WO 98/24374 | 6/1998 | (WO) | ............................. A61B/17/00 |
| WO 99/62408 | 12/1999 | (WO) | . |
| WO 00/07640 | 2/2000 | (WO) | . |
| WO 00/56223 | 9/2000 | (WO) | . |
| WO 00/56227 | 9/2000 | (WO) | . |

*Primary Examiner*—Gary Jackson
(74) *Attorney, Agent, or Firm*—Lyon & Lyon LLP

(57) ABSTRACT

Apparatus and methods are provided for use in sealing a vascular puncture site. The invention comprises an introducer sheath with an integrated closure component. The closure component includes an advanceable resilient spring clip with an expanded delivery configuration in which opposing sides do not contact one another, and an unstressed deployed configuration, in which opposing sides close towards one another. The clip is advanced along the sheath until it pierces opposing sides of a vessel wall at a puncture site. The sheath then is withdrawn, thereby causing the clip to resiliently return to its unstressed deployed configuration and draw opposing sides of the puncture together to seal the wound.

36 Claims, 9 Drawing Sheets

U.S. PATENT DOCUMENTS

| | | | |
|---|---|---|---|
| 5,222,974 | 6/1993 | Kensey et al. | 606/213 |
| 5,304,184 | 4/1994 | Hathaway et al. | 606/144 |
| 5,334,217 | 8/1994 | Das | 606/213 |
| 5,366,458 | 11/1994 | Korthoff et al. | 606/151 |
| 5,478,354 | 12/1995 | Tovey et al. | 606/219 |
| 5,527,322 | 6/1996 | Klein et al. | 606/144 |
| 5,674,231 | 10/1997 | Green et al. | 606/142 |
| 5,683,405 | 11/1997 | Yacoubian et al. | 606/158 |
| 5,695,505 | 12/1997 | Yoon | 606/157 |
| 5,782,844 | 7/1998 | Yoon et al. | 606/139 |
| 5,782,861 | 7/1998 | Cragg et al. | 606/216 |
| 5,810,846 | 9/1998 | Virnich et al. | 606/142 |
| 5,810,851 | 9/1998 | Yoon | 606/148 |
| 5,830,125 | 11/1998 | Scribner et al. | 606/139 |
| 5,879,366 | 3/1999 | Shaw et al. | 606/213 |
| 5,910,155 | 6/1999 | Ratcliff et al. | 606/213 |
| 5,984,934 | 11/1999 | Ashby et al. | 606/151 |
| 6,007,563 | 12/1999 | Nash et al. | 606/213 |
| 6,036,720 | 3/2000 | Abrams et al. | 606/213 |
| 6,077,281 | 6/2000 | Das | 606/151 |
| 6,077,291 | 6/2000 | Das | 606/213 |
| 6,080,182 | 6/2000 | Shaw | 606/213 |
| 6,080,183 | 6/2000 | Tsugita et al. | 606/213 |

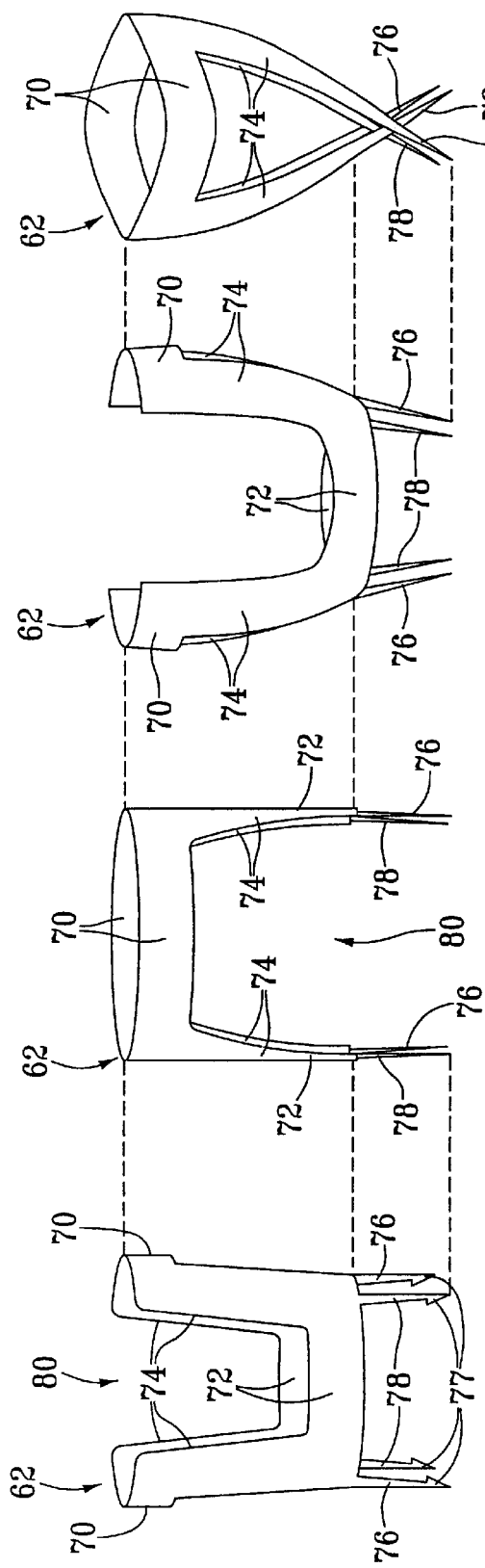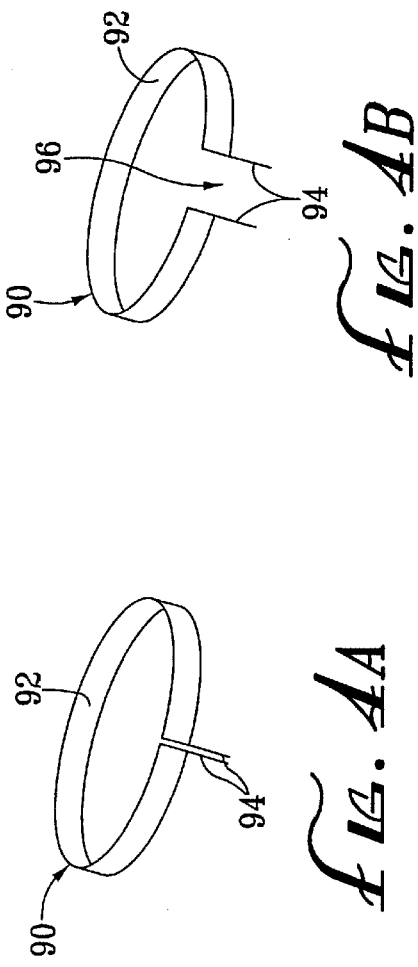

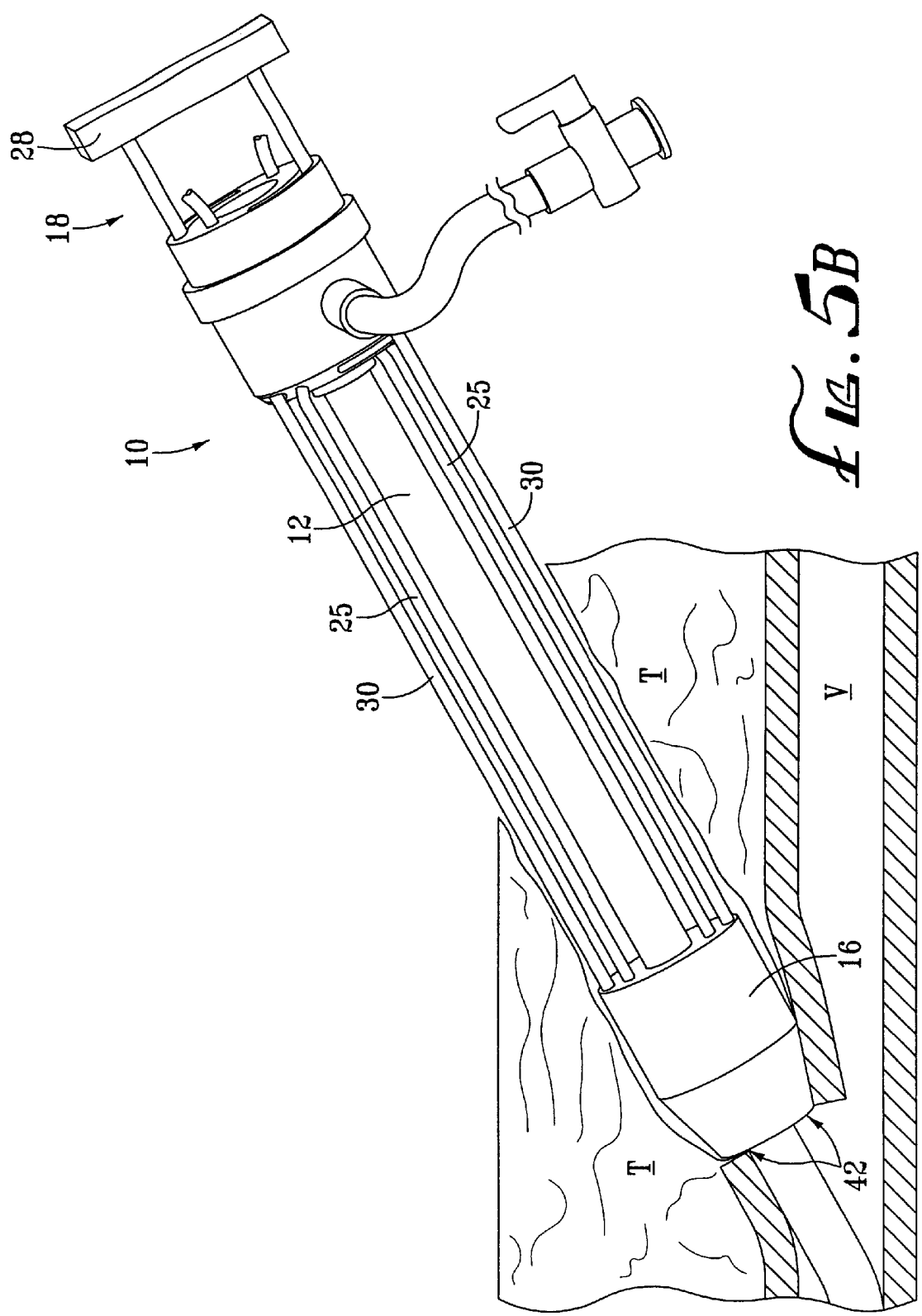

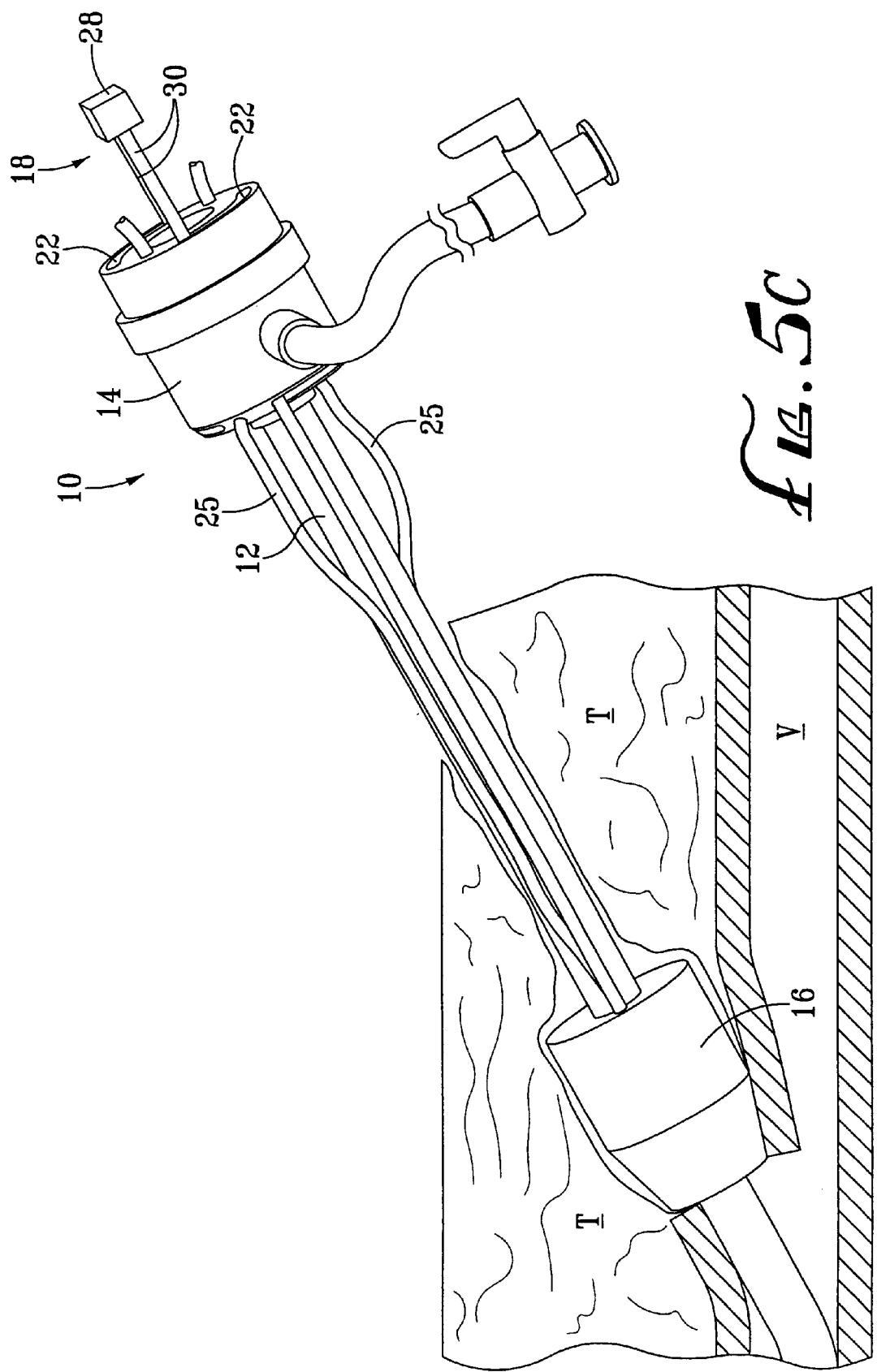

VASCULAR SHEATH WITH PUNCTURE SITE CLOSURE APPARATUS AND METHODS OF USE

This is a continuation application of Ser. No. 09/478,179, filed on Jan. 5, 2000.

FIELD OF THE INVENTION

The present invention relates to apparatus and methods for sealing an iatrogenic puncture in a vessel formed in conjunction with a diagnostic or therapeutic treatment. More particularly, the present invention provides apparatus comprising an introducer sheath including a puncture site closure device comprising an expandable clip with elastic memory.

BACKGROUND OF THE INVENTION

Catheterization and interventional procedures, such as angioplasty and stenting, generally are performed by inserting a hollow needle through a patient's skin and muscle tissue into the vascular system. A guide wire then is passed through the needle lumen into the patient's blood vessel. The needle is removed and an introducer sheath is advanced over the guide wire into the vessel. A catheter typically is passed through the lumen of the introducer sheath and advanced over the guide wire into position for a medical procedure. The introducer sheath therefore facilitates insertion of various devices into the vessel while minimizing trauma to the vessel wall and minimizing blood loss during a procedure.

Upon completion of the medical procedure, the catheter and introducer sheath are removed, leaving a puncture site in the vessel. Commonly, external pressure is applied until clotting and wound sealing occurs. However, this procedure is time consuming and expensive, requiring as much as an hour of a physician's or nurse's time, is uncomfortable for the patient, and requires that the patient be immobilized in the operating room, cathlab, or holding area. Furthermore, a risk of hematoma exists from bleeding prior to hemostasis.

Various apparatus have been developed for percutaneously sealing a vascular puncture by occluding or suturing the puncture site. For example, U.S. Pat. Nos. 5,192,302 and 5,222,974 to Kensey et al., describe the use of a biodegradable plug delivered through the introducer sheath into the puncture site. When deployed, the plug seals the vessel and provides hemostasis. Such devices have been slow to gain acceptance in the medical community, however, due to difficulties encountered in positioning the plug within the vessel. Moreover, the agents used to occlude the puncture site are animal-derived, typically collagen-based. Thus, a risk of adverse immunoresponse exists.

Another previously known technique comprises percutaneously suturing the puncture site with specialized apparatus. Such apparatus is described, for example, in U.S. Pat. No. 5,304,184 to Hathaway et al. While percutaneous suturing devices may be effective, a significant degree of skill may be required on the part of the practitioner. Because such devices are mechanically complex, they tend to be relatively expensive to manufacture.

Surgical staples and resilient clips for external skin wound closure are well known in the art, Examples include U.S. Pat. No. 5,026,390 to Brown and U.S. Pat. No. 5,683,405 to Yacoubian et al, which both describe resiliently deformable closure devices suitable for manual external application.

To reduce the cost and complexity of percutaneous puncture closure devices, such devices employing resilient clips or staples have been developed. U.S. Pat. No. 5,478,354 to Tovey et al. describes the use of resilient clips in conjunction with a trocar to close abdominal puncture wounds. U.S. Pat. No. 5,810,846 to Virnich et al. describes a specialized apparatus for closing a vascular puncture site with a plastically deformable clip. The apparatus preferably is advanced over a guide wire through a cannula to the surface of the puncture site, where the staple-like clips are delivered to close the wound.

U.S. Pat. No. 5,782,861 to Cragg et al. describes specialized apparatus for closing a puncture site with a detachable clip. The apparatus comprises a hollow shaft, having a distal end formed with one or more opposed pairs of resilient grasping prongs, that is advanced over a guide wire through a coaxial hollow tube to a position at the distal end of the tube just proximal of the puncture.

The grasping prongs are extended beyond the distal end of the tube to grasp the vessel on opposing sides of the puncture. The shaft then is partially retracted, causing the prongs to contract within the tube, thereby sealing the puncture site. Both of the devices described in the foregoing patents have the drawback that a separate device must be deployed through the introducer sheath to close the puncture site, thus prolonging the procedure. Moreover, both devices require relatively complex apparatus and involve time consuming manipulation to achieve hemostasis.

In view of the foregoing, it would be desirable to provide apparatus and methods suitable for vascular puncture closure that overcome the disadvantages of previously known devices.

It also would be desirable to provide apparatus and methods for vascular puncture closure that quickly and effectively achieve hemostasis.

It further would be desirable to provide vascular puncture closure apparatus and methods that do not require the introduction of additional apparatus at the completion of the catheterization procedure to achieve closure.

It still further would be desirable to provide apparatus and methods suitable for vascular puncture closure that do not introduce animal-derived material into the bloodstream.

It would be desirable to provide vascular puncture closure apparatus and methods that are safe, lower cost, and easy to use.

SUMMARY OF THE INVENTION

In view of the foregoing, it is an object of the present invention to provide vascular puncture closure apparatus and methods that overcome disadvantages of previously known devices.

It also is an object of this invention to provide apparatus and methods suitable for vascular puncture closure that quickly and effectively achieve hemostasis.

It is a further object of the present invention to provide apparatus and methods for vascular puncture closure that do not require the introduction of additional apparatus at the completion of the catheterization procedure to achieve closure.

It is another object of this invention to provide vascular puncture closure apparatus and methods that do not introduce animal-derived material into the bloodstream.

It is yet another object of the present invention to provide vascular puncture closure apparatus and methods that are safe, lower cost, and easy to use.

These and other objects of the present invention are accomplished by providing a vascular introducer sheath having an integrated wound closure component. The closure component consists of a resilient spring clip disposed on and advanceable over the exterior of the introducer sheath in an expanded delivery configuration until opposite sides of the clip pierce a vessel on opposite sides of a puncture site. The introducer sheath is then withdrawn, enabling the spring clip to contract to its unstressed deployed configuration, thereby drawing opposite sides of the puncture together and closing the wound. Means also are provided for confirming when the spring clip has engaged the vessel wall, thereby indicating to the surgeon that the clip may be deployed and the introducer sheath may be withdrawn. Alternative embodiments of the spring clip also are provided.

Advantageously, the closure component is inexpensively integrated into a standard introducer sheath, thereby eliminating the need for a separate closure device at the conclusion of a catheterization procedure. The present invention provides a quick, safe, effective and easy-to-use technique for wound closure that overcomes drawbacks of previously known devices. Methods of using the apparatus of the present invention also are provided.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIGS. 3A–3D are side views of the resilient clip of the present invention shown from different angles in an expanded delivery configuration and in an unstressed deployed configuration;

FIGS. 4A and 4B are isometric views of an alternative embodiment of the resilient surgical clip, constructed in accordance with the present invention and shown, respectively, in an unstressed deployed configuration and in an expanded delivery configuration; and FIGS. 5A–5F are side-sectional views of a vascular puncture site, illustrating a method of sealing the puncture site with the integrated vascular device of FIG. 1.

DETAILED DESCRIPTION OF THE INVENTION

The integrated vascular introducer sheath with closure component of the present invention overcomes disadvantages associated with previously known methods and apparatus for sealing a vascular puncture by providing a quick, simple, safe, lower cost, effective, and easy-to-use solution to wound closure. Apparatus constructed in accordance with the present invention provide vascular introduction and wound closure in a single device, eliminating the time and manipulation required to insert a separate closure device at the completion of a procedure.

Figure 1:
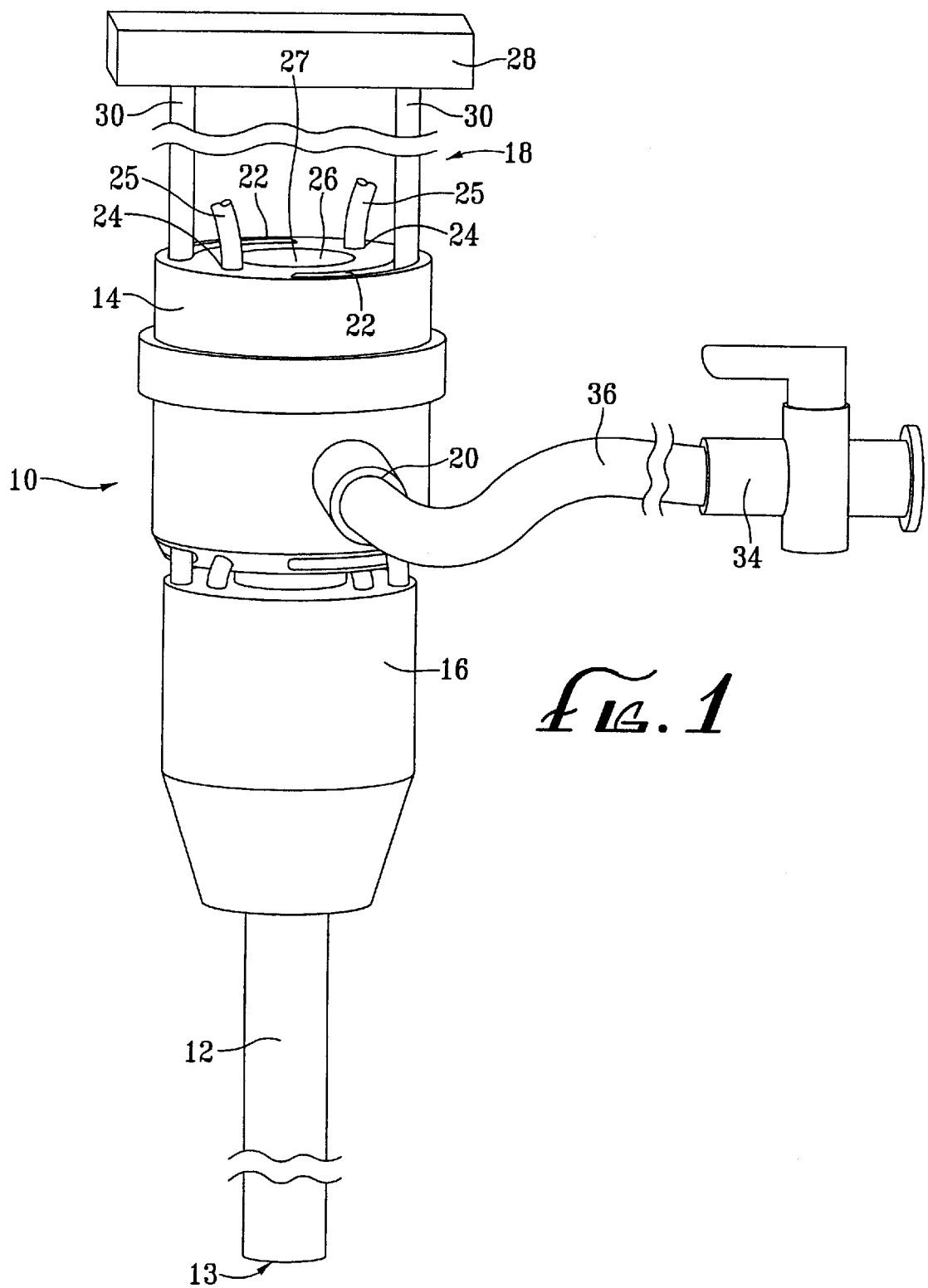
FIG. 1 is a side view of a vascular device constructed in accordance with the present invention.

Referring to FIG. 1, vascular device 10 comprises introducer sheath 12 coupled to hub 14, clip housing 16, and clip actuator 18.

Introducer sheath 12 comprises a material typically used for vascular introducer sheaths, such as polyethylene or nylon, and includes central lumen 13 through which other devices may be introduced in the vasculature, for example, to perform a diagnostic or interventional procedure such as angiography, angioplasty or stenting.

Hub 14 is mounted to the proximal end of introducer sheath 12 and includes side port 20, arc-shaped lumens 22, backbleed lumens 24, backbleed tubes 25, and device port 26. Device port 26 communicates with central lumen 13 of introducer sheath 12, and has self-sealing elastomeric membrane 27 disposed across it. Self-sealing membrane 27, which may comprise, e.g., latex or a biocompatible synthetic rubber, permits interventional devices to be introducer through device port 25 while preventing blood loss through central lumen 13. Side port 20 of hub 14 is in communication with central lumen 13, and is connected to hemostatic port 34 via biocompatible tubing 36.

Clip housing 16 includes an annular-shaped chamber that holds an elastically deformable clip. In accordance with the principles of the present invention, clip housing is slidably disposed on the exterior of introducer sheath 12 and is movable from a stowed position, adjacent hub 14, to a distal clip deployment position, where the spring clip is urged into engagement with tissue surrounding vascular puncture.

Clip actuator 18 comprises plunger 28 and rods 30, which are configured to slidably pass through arc-shaped lumens 22 of hub 14. The distal ends of rods 30 are mounted in clip housing 16, so that movement of plunger 28 causes corresponding proximal or distal movement of clip housing 16. As described in detail hereinafter, when plunger 28 is moved to its proximal-most position, clip housing is disposed adjacent to hub 14 and provides adequate clearance for interventional devices to be inserted device port 22 and central lumen 13 into the patient's vasculature. When moved to its distal-most position, plunger 28 causes rods 30 to urge clip housing 16 distally.

Figure 2:
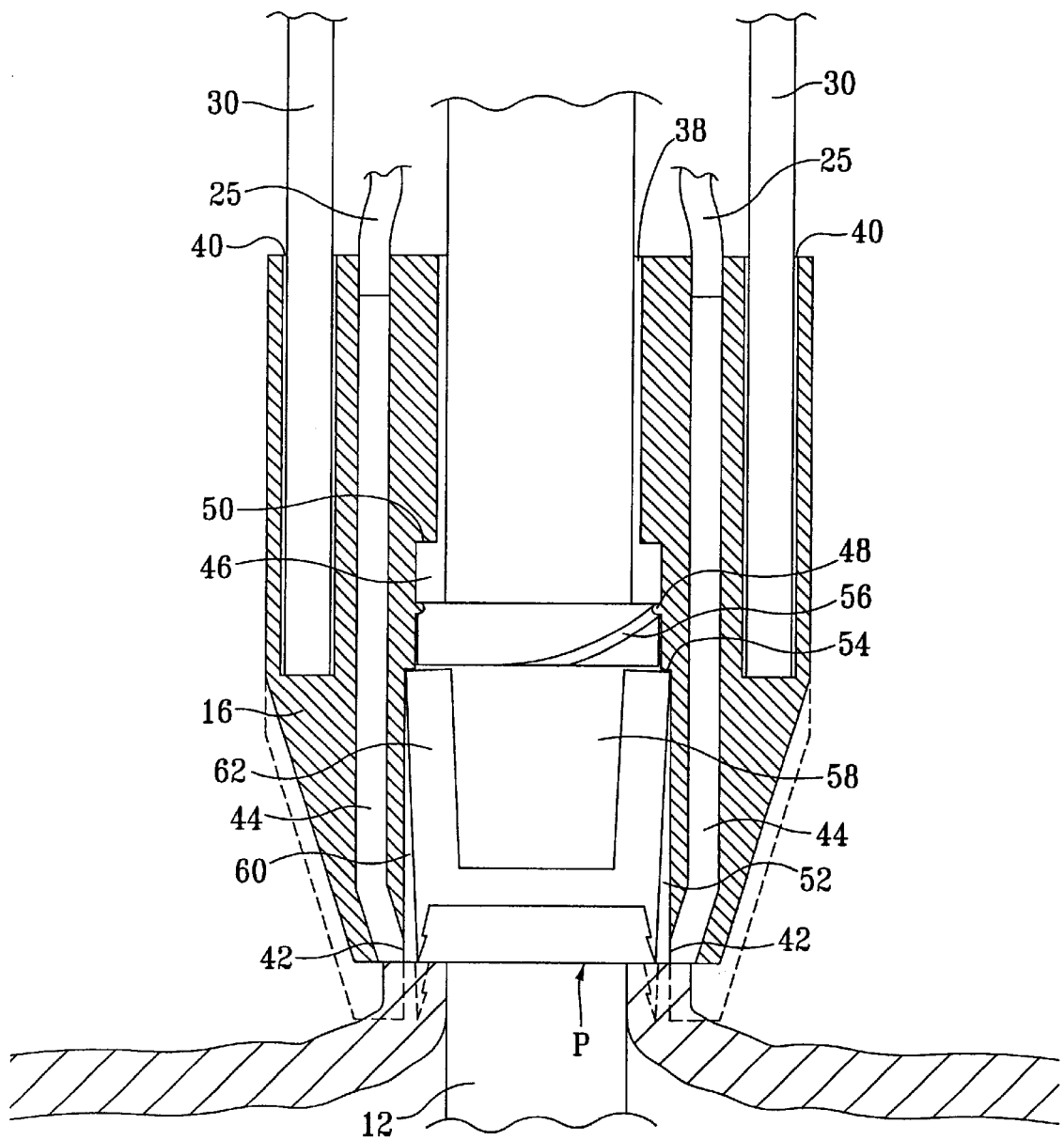
FIG. 2 is a cross sectional view of the closure component of the vascular device of FIG. 1.

Referring now also to FIG. 2, the closure component of vascular device 10 is described in greater detail. Clip housing 16 comprises bore 38 that slidably receives introducer sheath 12, bores 40 in which rods 30 are mounted, and backbleed indicator ports 42. Backbleed indicator ports 42 are coupled to backbleed tubes 25 via lumens 44. Housing 16 further comprises threaded bore 46 with male thread 48 and proximal ledge 50, and clip bore 52 with proximal ledge 54. Threaded bore 46 engages female thread 56 of clip expander 58. Clip expander 58 is slidably disposed on introducer sheath 12, and together with the portion of clip housing 16 surrounding the spring clip 62 forms annular chamber 60.

Spring clip 62 is stored in its expanded delivery configuration in annular chamber 60 so that it slidably passes over clip expander 58 until it abuts proximal ledge 54 of clip bore 52. In a delivery configuration of vascular device 10, the length of annular chamber 60, as measured from the distal end of clip expander 58 to proximal ledge 54, extends within the distal end of clip housing 16 for a sufficient distance to cover the length of clip 62. In this manner, clip housing 16 prevents snagging spring clip 62 from snagging on tissue during advancement of clip housing 16 to its deployed position, as described hereinbelow.

Rods 30 pass through arc-shaped lumens 22 of hub 14 and mounted in bores 40 of clip housing 16. Distal advancement of rods 30 causes clip housing 16, expander 58, and spring clip 62 to advance distally a corresponding distance relative to introducer sheath 12. When plunger 28 is moved to its distal-most position, rods 30 may be rotated within arc-shaped lumens 22 to rotate and advance clip housing 16 relative to clip expander 58. This motion causes clip housing 16 to advance distally along female thread 56 of clip expander 58 until the proximal end of the clip expander contacts proximal ledge 50 of threaded bore 46. Further rotation of rods 30 causes proximal ledge 54 to urge a tissue-engaging portion of spring clip 62 distally off of clip expander 58. With clip housing 16 positioned at a vascular puncture site P, rotation of rods 30 causes the tissue-engaging portion, illustratively spikes, to pierce the vessel wall, as seen in dotted profile in FIG. 2.

In alternative embodiments, plunger 28 and rods 30 may be removably coupled to clip housing 16, to permit unobstructed access to device port 26. In this embodiment, rods 30 may include teeth that may be rotated to fixedly engage bores 40 in clip housing 16.

As discussed hereinabove, backbleed indicator ports 42 are coupled to tubes 25 via blood lumens 44 that extend through clip housing 16. Backbleed tubes 25 are slidably disposed through backbleed lumens 24 of hub 14. When the distal end of clip housing 16 is advanced distally against the vessel wall at puncture P, blood enters blood indicator ports 42 and exits tubes 25, providing visual confirmation to the surgeon that the distal end of clip housing 16 is positioned adjacent to the vessel wall. Backbleed tubes 25 thus enable the surgeon to determine when clip housing 16 has been advanced sufficiently to permit clip deployment, while reducing the risk that the clip is either deployed short of the puncture site or extended into the vessel.

Still referring to FIG. 1, in conjunction with clip deployment, a bioglue or tissue sealant may be delivered through hemostatic port 34, tubing 36, port 20 and central lumen 13 of introducer sheath 12 to vascular puncture P to further help seal the vessel after deployment of clip 62. Alternatively, the bioglue or tissue sealant may be delivered through the backbleed path described above.

Referring now to FIGS. 3A–3D, an illustrative spring clip 62 constructed in accordance with the principles of the present invention is described in greater detail. FIG. 3B is a side view of the clip of FIG. 3A rotated 90 degrees, wherein clip 62 is in an expanded delivery configuration. Clip 62 comprises an annular device having upper members 70 joined to lower members 72 by legs 74 to form lumen 80. Outer spikes 76 and inner spikes 78 are connected to lower members 72, and act as elongated tissue-engaging members. Clip 62 is elastically expanded by advancing introducer sheath 12 or clip expander 58 through lumen 80.

Upon removal of the introducer sheath, spring clip 62 resiliently returns to its unstressed deployed configuration, illustrated in FIGS. 3C and 3D, where FIG. 3C corresponds to the view of FIG. 3A and FIG. 3D corresponds to the view of FIG. 3B. When removed from the exterior of introducer sheath 12, spring clip 62 resumes its deployed shape, in which the opposing sides of the clip come together until lower members 72 contact one another, and outer spikes 76 cross inner spikes 78. As depicted in FIG. 3A, clip 62 also may optionally comprise engagement means 77 to securely engage the vessel being closed. Engagement means 77 may, for example, comprise barbs or hooks.

Clip 62 is preferably fabricated from a superelastic material, such as a nickel-titanium alloy, but may comprise any material with sufficient resilience to elastically expand for delivery over sheath 12 and fit within annular chamber 60 of clip housing 16. Clip 62 also may be fabricated from a bioabsorbable material or a combination bioabsorbable and elastically expandable material.

FIGS. 4A and 4B illustrate an alternative embodiment of the resilient spring clip of the present invention, wherein clip 90 comprises hoop 92 and opposing spikes 94. In FIG. 4A, clip 90 is depicted in the unstressed, deployed configuration, in which opposing spikes 94 contact one another, whereas in FIG. 4B clip 90 is depicted in the expanded, delivery configuration, in which opposing spikes 94 are separated by gap 96. Clip 90 is elastically expanded in a manner similar to clip 62 by advancement over introducer sheath 12, and preferably also is fabricated from the materials described hereinabove.

Figure 5A:
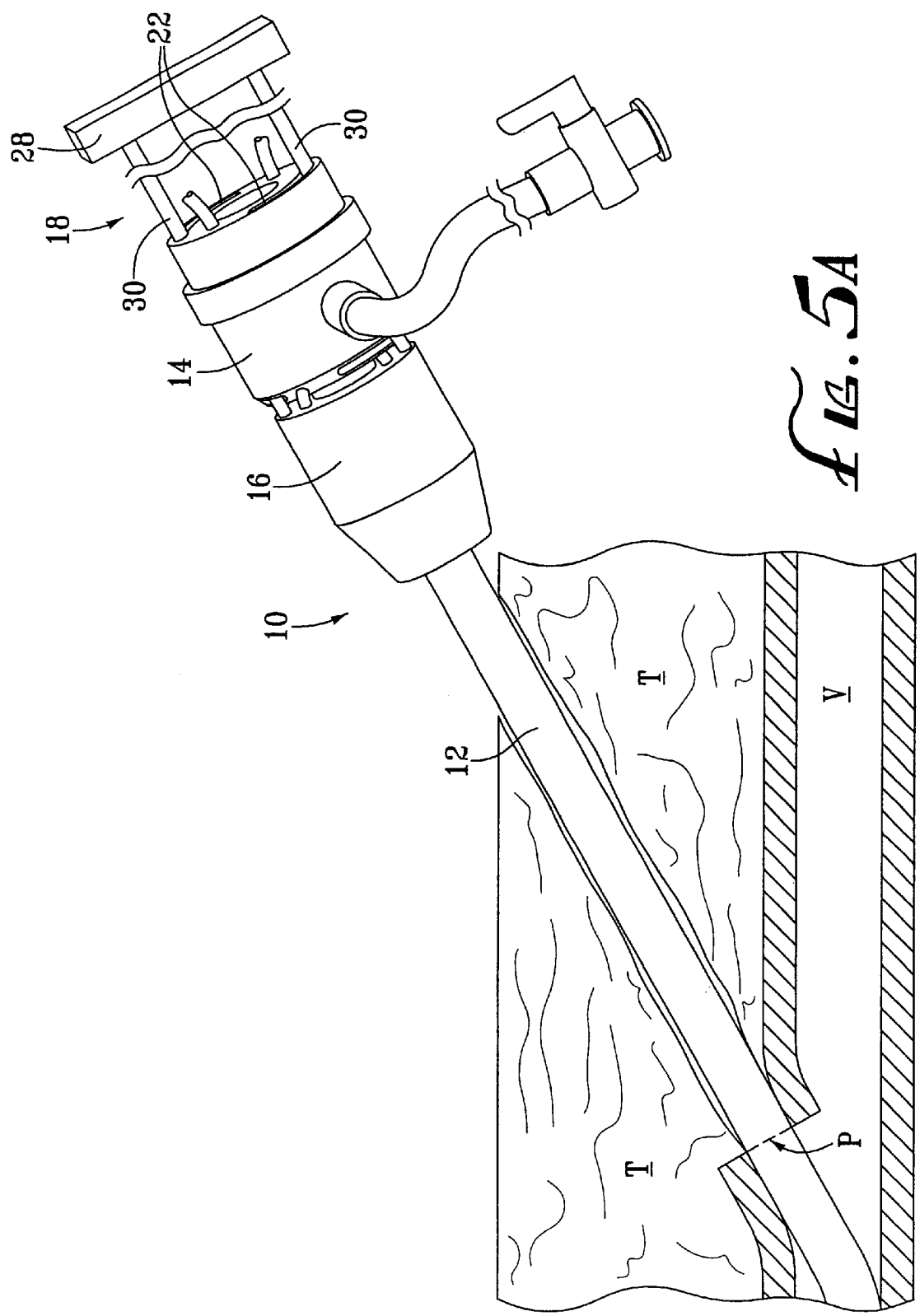

Referring now to FIGS. 5A–5F, in conjunction with FIGS. 1–3, methods of using vascular device 10 are described. In FIG. 5A, introducer sheath 12 has been advanced through skin, fat, and muscle tissue T into vessel V, through vascular puncture P, which is formed in accordance with well-known techniques. With plunger 28 and rods 30 in the proximal-most, fully retracted position, an interventional procedure then is performed by introducing one or more interventional devices, e.g. angioplasty balloons, stent delivery systems, atherectomy devices, etc., through device port 26 and lumen 13 of introducer sheath 12 in accordance with well-known techniques. Side port 20 may be used to infuse fluids, e.g., contrast agents or medications, into the vessel through introducer sheath 12 during the interventional procedure.

Upon completion of the procedure, vascular device may be advantageously used to close vascular puncture P. At this point, clip actuator 18, housing 16, clip expander 58, and clip 62 are disposed in the proximal-most position adjacent to hub 14, as depicted in FIG. 5A.

As illustrated in FIG. 5B, clip actuator 18 then is advanced by urging plunger 28 in the distal direction, thus causing rods 30 to slide through arc-shaped lumens 22 of hub 14 and advance clip housing 16. Continued distal advancement of plunger 28 causes the distal end of clip housing 16 to abut against the exterior of the vessel, so that back bleed indicator ports 42 of clip housing 16 directly communicate with the puncture wound. The presence of pressure in the vessel higher than atmospheric pressure causes blood to pass through indicator ports 42, blood lumens 44, and exit through the proximal ends of tubes 25, thus confirming that clip housing 16 is positioned at the puncture site and should not be advanced further.

In FIG. 5C, with clip housing 16 held immobile, clip actuator 18 is rotated clockwise within arc-shaped lumens 22 so that rods 30 rotate and advance clip housing 16 with respect to clip expander 58 (see FIG. 2). Specifically, ledge 54 of housing 16 contacts the proximal end of clip 62 and drives the clip distally so that its tissue-engaging members, spikes 76 and 78, contact and pierce the wall of vessel V at points around the puncture site, as discussed hereinabove with respect to FIG. 2.

Figure 5D:
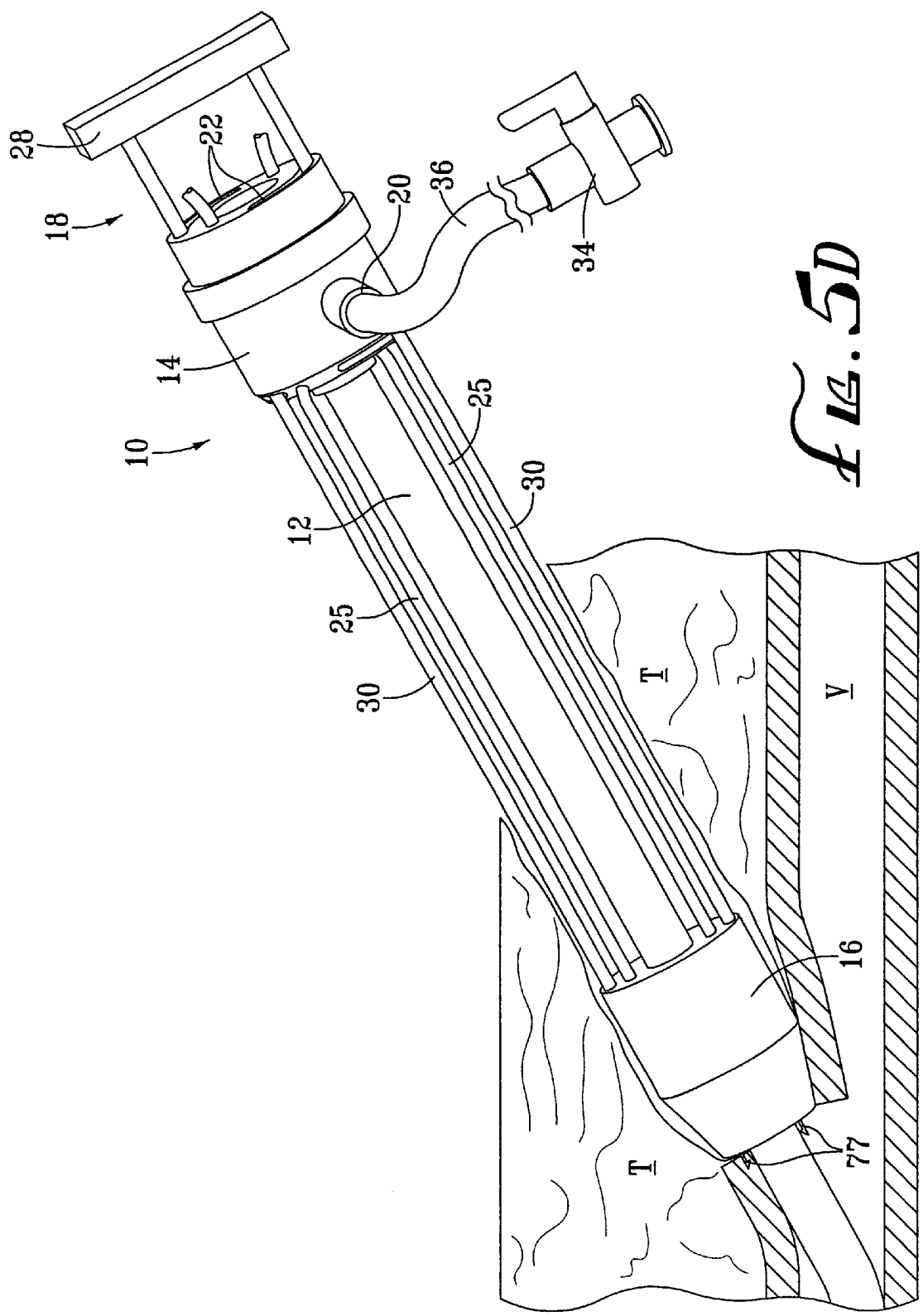

Once the spikes have pierced the vessel wall, clip actuator 18 is rotated counterclockwise within arc-shaped lumens 22 to retract clip housing 16, via threaded bore 46, along clip expander 58. The tissue-engaging members of clip 62 retain the clip within the wall of vessel V while the housing retracts, as shown in FIG. 5D.

Figure 5E:
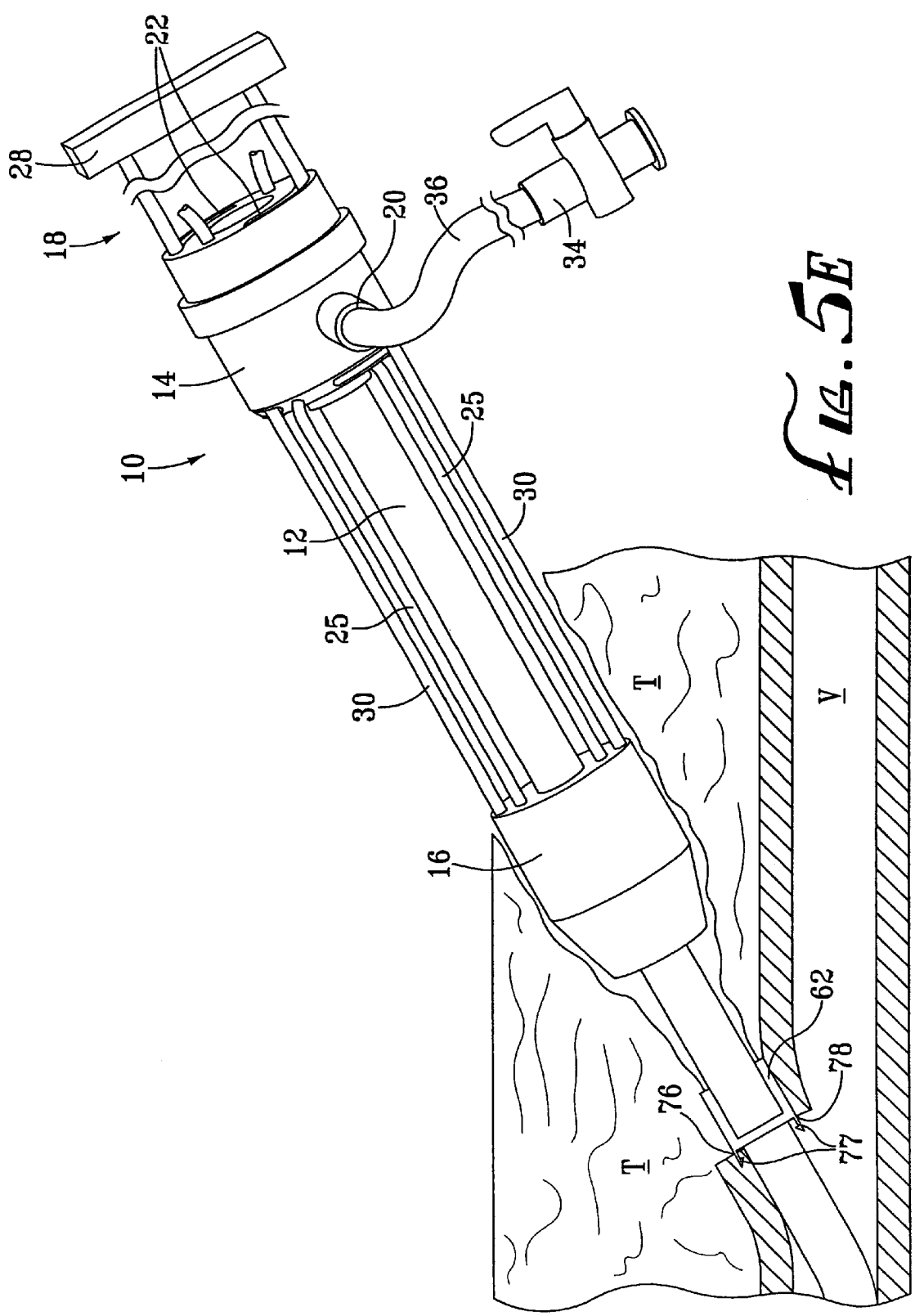

In FIG. 5E, with clip 62 engaged with the vessel wall, clip housing 16 and clip expander 58 are withdrawn proximally by proximally withdrawing actuator 18, thereby causing clip 62 to slide off of clip expander 58. In FIG. 5E, spike 78 is embedded in tissue not shown, because that tissue lies within the plane of the cross section.

Figure 5F:
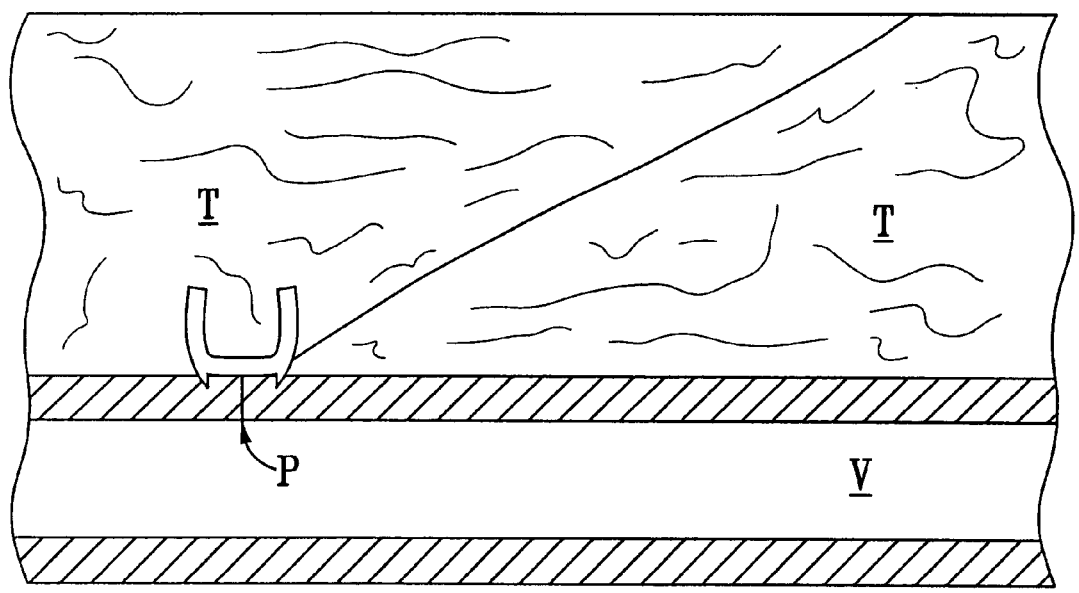

Vascular device 10 then is withdrawn from the vessel wall. Once introducer sheath 12 is removed from lumen 80 of clip 62, the clip rotates relative to the vessel wall, as shown in FIG. 5F, and returns to its unstressed, deployed configuration, thus drawing opposite sides of puncture P together to seal the puncture. At this point, a suitable biocompatible bioglue or tissue sealant optionally may be injected into the puncture tract, as discussed hereinabove, through device port 26 or side port, to aid in sealing vascular puncture P. Alternatively, the bioglue or tissue sealant may be delivered through the backbleed path described above.

Although preferred illustrative embodiments of the present invention are described above, it will be evident to one skilled in the art that various changes and modifications may be made without departing from the invention. For example, with minor modifications, vascular device 10 may be configured to carry spring clip 90 of FIGS. 4, or any of a variety of alternative expandable resilient clips. It is intended in the appended claims to cover all such changes and modifications that fall within the true spirit and scope of the invention.

What is claimed is:

1. An apparatus for closing a puncture communicating between a patient's skin and a vessel, comprising:
    a tubular member having proximal and distal regions and an exterior surface;
    a housing slidably disposed on the exterior surface of the tubular member, the housing including a portion defining a chamber; and
    a clip releasably disposed within the chamber, the clip being expandable from a deployed configuration wherein opposing sides of the clip are directed inwards towards one another, and a delivery configuration, in which the clip is accepted within the chamber.

2. The apparatus of claim 1, further comprising an actuator for deploying the clip from the chamber into engagement with tissue surrounding the puncture to close the puncture.

3. The apparatus of claim 2, wherein the actuator comprises an elongated member coupled to the housing.

4. The apparatus of claim 2, wherein the actuator is configured for advancing the housing from the proximal region to the distal region of the tubular member.

5. The apparatus of claim 2, wherein the actuator is detachably coupled to the housing.

6. The apparatus of claim 1, further comprising a backbleed indicator port on the housing for indicating a position of the housing relative to the vessel.

7. The apparatus of claim 1, further comprising a side port for introducing fluids into a lumen of the tubular member.

8. The apparatus of claim 1, wherein the tubular member comprises an introducer sheath comprising a lumen for advancing therapeutic or diagnostic instruments therethrough into the vessel.

9. The apparatus of claim 1, wherein the clip is biased to the deployed configuration and is resiliently expandable to the delivery configuration.

10. The apparatus of claim 1, wherein the clip comprises a tubular member from which a plurality of elongated tissue-engaging elements extend.

11. The apparatus of claim 10, further comprising barbs on the tissue-engaging elements.

12. The apparatus of claim 10, wherein the tubular member further comprises a plurality of elongated legs having proximal and distal ends, a plurality of upper members connecting respective proximal ends of the elongated legs, and a plurality of lower members interconnecting respective alternating distal ends of the elongated legs, wherein the plurality of tissue-engaging members project from the plurality of lower members.

13. The apparatus of claim 1, wherein the clip is bioabsorbable.

14. The apparatus of claim 1, further comprising an expander having an exterior surface, the expander slidably and coaxially disposed on the exterior surface of the introducer sheath, the housing coaxially disposed on and cammingly engaged with the expander for expanding the clip when it is deployed from the chamber.

15. A method for closing a puncture communicating between a patient's skin and a vessel, the method comprising:
    advancing a tubular member through the puncture into the vessel, the tubular member comprising a housing disposed on an exterior surface of the tubular member;
    advancing the housing distally along the exterior surface of the tubular member into the puncture, the housing having a clip therein;
    engaging tissue adjacent the puncture with tissue-engaging elements on the clip; and
    drawing the tissue-engaging elements towards one another to close the puncture.

16. The method of claim 15, wherein the tubular member comprises an introducer sheath, and wherein the method further comprises introducing one or more devices through the introducer sheath into the blood vessel.

17. The method of claim 16, wherein the one or more devices are selected from the group consisting of an angioplasty balloon, an atherectomy device, and a stent delivery device.

18. The method of claim 16, further comprising performing an interventional procedure within the patient's body using the one or more devices introduced through the introducer sheath into the vessel.

19. The method of claim 15, wherein the step of drawing the tissue-engaging elements towards one another comprises withdrawing the tubular member from the puncture.

20. The method of claim 19, wherein the tissue-engaging elements are biased to resiliently move towards one another from a delivery configuration to a deployed configuration when the tubular member is withdrawn from the puncture.

21. The method of claim 15, wherein an actuator is used to advance the housing along the exterior surface of the tubular member into the puncture.

22. The method of claim 21, wherein the actuator is coupled to the housing before advancing the housing.

23. The method of claim 22, wherein the tubular member comprises a hub having a bore, and wherein a portion of the actuator is inserted into the bore of the hub before advancing the housing.

24. The method of claim 15, wherein the step of engaging tissue comprises deploying the clip from the housing.

25. The method of claim 15, wherein the housing comprises an expander for expanding the clip, and wherein the step of engaging tissue comprises advancing the clip relative to the expander to deploy the clip from the housing.

26. The method of claim 15, further comprising delivering a tissue sealant into the puncture.

27. The method of claim 15, wherein the housing comprises backbleed indicator ports, and wherein the housing is advanced distally along the tubular member until blood from the vessel flows through the backbleed indicator ports to a proximal region of the tubular member.

28. The method of claim 15, wherein the step of engaging tissue comprises engaging a wall of the vessel with the tissue-engaging elements.

29. The method of claim 28, wherein the step of engaging a wall of the vessel comprises piercing the wall of the vessel with the tissue-engaging elements.

30. A method for closing a puncture communicating between a patient's skin and a vessel, the method comprising:
    advancing a tubular member through the puncture into the vessel, the tubular member comprising a housing disposed on an exterior surface of the tubular member, the housing having a clip therein;

advancing the housing distally along the exterior surface of the tubular member into the puncture until tissue-engaging elements on the clip engage tissue adjacent the vessel; and drawing the tissue-engaging elements towards one another to close the puncture.

31. The method of claim 30, wherein the tubular member comprises an introducer sheath, and wherein the method further comprises introducing one or more devices through the introducer sheath into the blood vessel.

32. The method of claim 30, wherein the step of drawing the tissue-engaging elements towards one another comprises withdrawing the tubular member from the puncture.

33. The method of claim 32, wherein the tissue-engaging elements are biased to resiliently move towards one another from a delivery configuration to a deployed configuration when the tubular member is withdrawn from the puncture.

34. The method of claim 30, wherein the housing is advanced until the tissue-engaging elements engage a wall of the vessel.

35. The method of claim 30, wherein the housing is advanced until the tissue-engaging elements pierce a wall of the vessel.

36. The method of claim 30, wherein the step of advancing the housing comprises deploying the clip from the housing.

* * * * *